United States Patent
Fox et al.

(10) Patent No.: US 8,416,919 B2
(45) Date of Patent: Apr. 9, 2013

(54) APPARATUS TO FACILITATE CAPTURING SAMPLES AS PERTAIN TO AN OBJECT TO BE IMAGED AND CORRESPONDING METHOD

(75) Inventors: Timothy R. Fox, Chicago, IL (US); David T. Nisius, Des Plaines, IL (US)

(73) Assignee: Varian Medical Systems, Inc., Palo Alto, CA (US)

( * ) Notice: Subject to any disclaimer, the term of this patent is extended or adjusted under 35 U.S.C. 154(b) by 533 days.

(21) Appl. No.: 12/544,274

(22) Filed: Aug. 20, 2009

(65) Prior Publication Data

US 2011/0044493 A1 Feb. 24, 2011

(51) Int. Cl.
*H05G 1/70* (2006.01)
*G01N 23/04* (2006.01)
*G01N 23/10* (2006.01)

(52) U.S. Cl. ............ 378/92; 378/19; 378/57; 378/62; 378/98.8; 378/146

(58) Field of Classification Search .......... 378/19, 378/57, 62, 92, 98.8, 146
See application file for complete search history.

(56) References Cited

U.S. PATENT DOCUMENTS

| | | | |
|---|---|---|---|
| 6,236,709 B1 | 5/2001 | Perry et al. | |
| 7,221,732 B1* | 5/2007 | Annis | 378/57 |
| 7,233,644 B1* | 6/2007 | Bendahan et al. | 378/57 |
| 7,319,737 B2* | 1/2008 | Singh | 378/57 |
| 7,362,847 B2* | 4/2008 | Bijjani | 378/57 |
| 2003/0147489 A1 | 8/2003 | Bijjani et al. | |
| 2007/0025505 A1 | 2/2007 | Bjorkholm | |
| 2007/0133744 A1* | 6/2007 | Bijjani | 378/57 |
| 2007/0237293 A1* | 10/2007 | Singh | 378/57 |
| 2007/0237294 A1 | 10/2007 | Hoff et al. | |

OTHER PUBLICATIONS

Extended European Search Report from related EP Application No. 10172488.8; dated Oct. 31, 2011; 7 pages.

\* cited by examiner

*Primary Examiner* — Thomas R Artman
(74) *Attorney, Agent, or Firm* — Fitch, Even, Tabin & Flannery LLP (57) ABSTRACT

One facilitates capturing samples as pertain to an object to be imaged by providing N pulsed sampling chains (where N is an integer greater than 1) where these sampling chains are in planes substantially parallel to one another and are substantially equidistant from adjacent others by a given distance. By one approach, the ratio of this given distance to a desired sample interval is approximately an integer that is relatively prime to N. So configured, a complete set of samples of the object can be captured by the sampling chains in a single pass notwithstanding that the object and the sampling chains are moving quickly with respect to one another.

19 Claims, 4 Drawing Sheets

FIG. 1

201 — PROVIDE N PULSED SAMPLING CHAINS WHERE:
- THE SAMPLING CHAINS ARE IN PLANES SUBSTANTIALLY PARALLEL TO EACH OTHER
- THE SAMPLING CHAINS ARE SUBSTANTIALLY EQUIDISTANT FROM EACH OTHER BY A GIVEN DISTANCE
- A RATIO OF THE GIVEN DISTANCE TO A DESIRED SAMPLE INTERVAL IS APPROXIMATELY AN INTEGER THAT IS RELATIVELY PRIME TO N

SUCH THAT A COMPLETE SET OF SAMPLES OF THE OBJECT CAN BE CAPTURED BY THE SAMPLING CHAINS IN A SINGLE PASS NOTWITHSTANDING THAT THE OBJECT AND THE SAMPLING CHAINS ARE MOVING QUICKLY WITH RESPECT TO ONE ANOTHER

202 — DETERMINE A RELATIVE VELOCITY AS BETWEEN THE OBJECT AND THE SAMPLING CHAINS

203 — USE THE RELATIVE VELOCITY TO DETERMINE WHEN TO PULSE THE SAMPLING CHAINS TO CAPTURE CORRESPONDING SAMPLES OF THE OBJECT

204 — USE THE SAMPLING CHAINS TO CAPTURE THE COMPLETE SET OF SAMPLES IN A CORRESPONDING CHRONOLOGICAL ORDER

205 — REORDER THE SAMPLES IN OTHER THAN THE CHRONOLOGICAL ORDER OF CAPTURE TO PROVIDE REORDERED SAMPLES

206 — USE THE REORDERED SAMPLES TO PROVIDE AN IMAGE OF THE OBJECT

APPARATUS TO FACILITATE CAPTURING SAMPLES AS PERTAIN TO AN OBJECT TO BE IMAGED AND CORRESPONDING METHOD

TECHNICAL FIELD

This invention relates generally to high-energy imaging systems.

BACKGROUND

Imaging systems that utilize high energy radiation (such as x-rays) to sample an object to be imaged are known in the art. Many such systems employ one or more high-energy sources that form corresponding fan beams of high energy. One or more detectors then detect the extent to which the object interacts with this high energy (for example, by absorbing some portion of that energy). By providing relative motion of the source/detector with respect to the object a series of such images can be assembled to form a composite image of the object.

Unique problems arise when attempting to employ such approaches when the source/detector and the object move relatively quickly with respect to one another. For example, such an approach is theoretically applicable for use in sampling a fast-moving object such as a railroad train. A practical realization of this approach, however, encounters numerous significant obstacles. As one example in this regard, the pulse periodicity of a single energy source may be too slow to permit a train to be completely sampled as the train speeds past the imaging system. Consider that a typical sampling requirement might be a 5 mm sample pitch. With a 1 ms sample period (admittedly high but nevertheless achievable) and a 15 m/s velocity, however, the spacing between samples for one sampling chain 100 is 15 mm. If the detector width demagnified into the object plane is 5 mm, this single sampling chain 101 would then have 5 mm wide vertical bands with 10 mm blank spaces separating them. The resultant composite image would therefore be missing ⅔rds of the train.

Using a plurality of sources/detectors in such a case to capture the remainder of the object, in turn, also encounters numerous speed-related problems. In particular, one can quickly conclude that an inappropriately large number of such sampling chains are potentially required in order to attempt capturing a complete set of samples for a fast-moving object and even this may prove insufficient; there may still be unacceptable gaps in the information so captured. This can lead to a variety of intractable problems including a physical inability to accommodate all of the sampling chains, a practical inability to make the financial investment necessary to acquire or operate the sampling chains, and so forth.

BRIEF DESCRIPTION OF THE DRAWINGS

The above needs are at least partially met through provision of the apparatus to facilitate capturing samples as pertain to an object to be imaged and corresponding method described in the following detailed description, particularly when studied in conjunction with the drawings, wherein.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, one can facilitate capturing samples as pertain to an object to be imaged by providing N pulsed sampling chains (where N is an integer greater than 1) where these sampling chains are in planes substantially parallel to one another and are substantially equidistant from adjacent others by a given distance. By one approach, the ratio of this given distance to a desired sample interval is approximately an integer that is relatively prime to N. So configured, a complete set of samples of the object can be captured by the sampling chains in a single pass notwithstanding that the object and the sampling chains are moving quickly with respect to one another.

These teachings will further support using these sampling chains, so configured, to capture a complete set of samples in a corresponding chronological order and then reorder those samples in other than the chronological order of capture. These reordered samples can then be used to provide an image of the object.

These teachings will also support, if desired, determining a relative velocity as between the object and the sampling chains and then using this relative velocity to determine when to pulse the sampling chains to capture the aforementioned samples of the object. By one approach, the relative velocity can be determined by measuring this parameter (using, for example, an appropriate velocity-measuring component).

These teachings will also support, if desired, using more than one detector array in a given sampling chain. For example, a given sampling chain (or each of the sampling chains) can have a side-by-side detector array. Such a configuration can improve the available resolution for the resultant image.

So configured, these teachings permit a fast-moving object such as a train to be completely sampled while using only a modest number of sampling chains. This, in turn, serves to limit the corresponding economic expenditures associated with acquiring, installing, and maintaining the sampling chains in a manner that greatly improves the opportunity for a given end user to in fact acquire and utilize such capabilities. These teachings are readily employed with existing sampling chain technology and methodologies and hence can greatly leverage the practical usability and value of such knowledge. These teachings are also highly scalable and will support usage in a wide variety of application settings and with objects traveling at any of a wide variety of high speeds.

These and other benefits may become clearer upon making a thorough review and study of the following detailed description. Referring now to the drawings, illustrative processes and apparatuses that are compatible with many of these teachings will now be presented.

Figure 1:
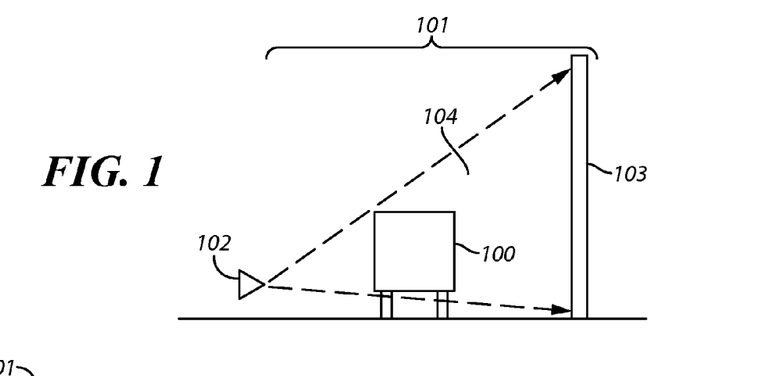
FIG. 1 comprises a front-elevational schematic view as configured in accordance with various embodiments of the invention.

With initial reference to FIG. 1, a useful illustrative application setting will first be described. Those skilled in the art will understand and recognize that these teachings are not necessarily limited, however, to such a setting. In this example, a train 100 of indeterminate length approaches the viewer at a relatively high speed (somewhere in the range, for example, of 10 miles per hour to 100 miles per hour or faster). The train 100 passes through a plurality of sampling chains 101 (with only one being shown). As used herein, the expression "sampling chain" will be understood to refer to a pulsed high-energy source 102 such as an x-ray source and a corresponding detector 103. In this illustrative example the detector 103 comprises a vertical detector array. Such sources and detector arrays are well known in the art and require no further elaboration here.

So configured, a pulsed beam 104 of x-ray energy as emitted by the x-ray source 102 will be detected by the detector 103. A portion of this beam 104 will interact with the train 100. The extent of this interaction between the beam 104 and the train 100 as detected by the detector 103 provides information that can be utilized to develop a corresponding image of the train. In this illustrative example the beam 104 comprises a fan beam that interacts with a vertical detector array having a relatively thin width (such as 5 mm or so). As a result, each such pulsed beam 104 yields only a relatively narrow line of image information regarding the train 100.

Those skilled in the art will understand that, with a pulsed source 102, the fastest sampling possible in a digital radiography system is one image sample per pulse period. Accordingly, in the direction of motion the distance moved between samples is the product of velocity and sample period. Therefore, when the pulse width is very short (as may correspond, for example, to a low duty factor) each sample may cover a relatively short length of the object.

In an application setting as shown, the sampling is different in two perpendicular directions: one direction along the detector array 103 and the other direction in the direction of motion. Sampling is described by sample pitch and sample size in these two directions. The detector array 103 typically comprises a set of evenly-spaced rectangular elements. The samples in the object plane (for this parallel geometry) are assumed to be identical in size; each is a rectangle corresponding to the demagnified size of a detector element. (In a different geometry, such as a detector arc, the magnification factor varies along the array and the samples in the object plane vary accordingly.)

For such geometry the sample pitch in the array direction is simply the demagnified pitch (center-to-center spacing) of the detector array. In the motion direction, the sample pitch is the product of the velocity and sample period, independent of magnification. When interested in several parallel planes within the object, the sample pitch along the detector array in a plane varies with plane position (parallax), but the sample pitch in the motion direction is independent of plane position. The sample size, however, varies in both directions with plane position. These two directions are referred to herein as "vertical" (along the detector array 103) and "horizontal" (parallel to motion), corresponding to a train 100 moving on a horizontal track (not shown) past a vertical detector array.

The sample pitch in an object plane is determined by the above discussion, but the actual area in the object plane in each detector sample is increased further by two factors: the finite size (spatial) and the finite pulse width (temporal) of the source 102. The source size blurs both dimensions of the sample while the pulse width blurs only the horizontal size. With linear accelerators, the pulse width is typically about 4 µs, so even with a very high object velocity (for example, 15 m/s or 54 km/hr) this increases the horizontal dimension by only 0.06 mm, which is negligible. Typical detector sizes are between 1 and 10 mm in both directions though of course the described teachings can be employed with other detector sizes.

In a simple digital radiography system, the velocity and sample period are chosen to give a horizontal sample pitch (independent of the object plane) comparable to the vertical sample pitch (in a nominal object plane) and the detector element sizes (demagnified to the object plane) are roughly equal to these pitches. Resampling these data assembles a final image with square pixels in a specified nominal image plane.

There are practical limits, however, to the minimum pulse period that corresponds to the maximum pulse repetition frequency (PRF). This, in turn, limits the maximum velocity for a good image. At high velocity, the horizontal spacing between samples becomes much larger than the horizontal dimension of the sample, and vertical bands of the object (between samples) are not included in the image.

At high velocity, with a pulsed source and single detector array, the strobe effect of the narrow pulses typically yields widely-spaced vertical bands of information along the horizontal motion direction. Each of these bands, however, is a high-resolution sample that is complete in the vertical direction and well-defined in the horizontal direction (governed by the physical size of the detector). To fill in the missing bands, these teachings further use a reasonable number of additional sampling chains 101. To do this efficiently and to maintain the number of additional sampling chains 101 at a reasonable number, these teachings provide for carefully choosing the distance between adjacent sampling chains.

Figure 2:
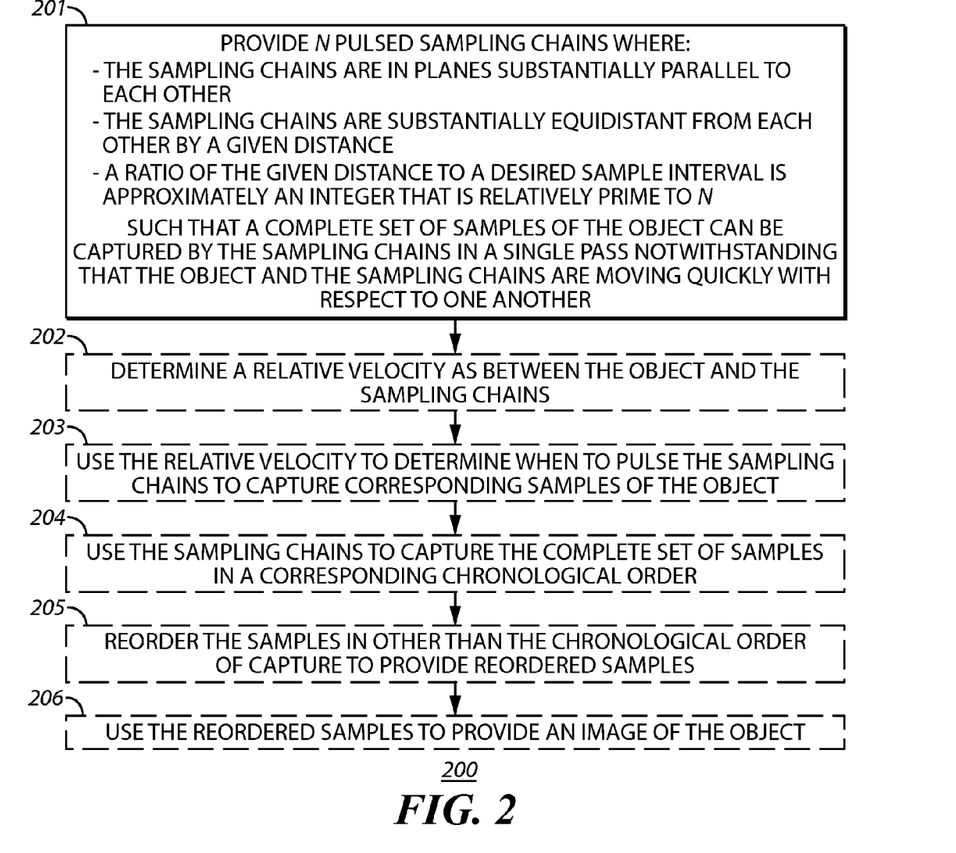
FIG. 2 comprises a flow diagram as configured in accordance with various embodiments of the invention.

With these points in mind, and referring now to FIG. 2, an illustrative process 200 that is compatible with many of these teachings will now be presented. This process 200 generally serves to facilitate capturing samples as pertain to an object to be imaged.

This process 200 includes the step 201 of providing N pulsed sampling chains 101. As used herein, "AP" is an integer greater than 1. One goal of these teachings is to maintain N at a relatively low number in order to achieve a viable economic result. With reference to both FIGS. 2 and 3, these sampling chains 101 are in planes that are substantially parallel to each other. These sampling chains 101 are also disposed substantially equidistant from each other by a given distance D (this referring, of course, to adjacent sampling chains 101).

Figure 3:
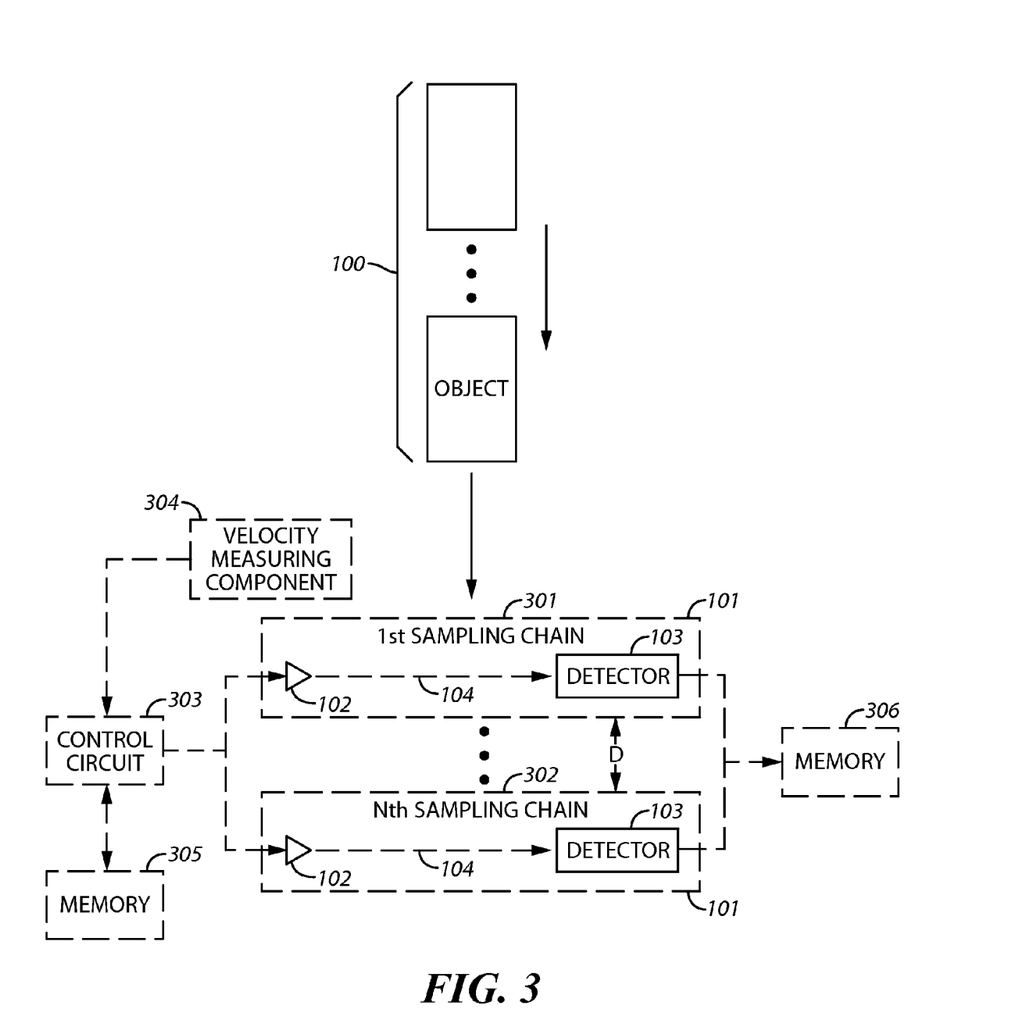
FIG. 3 comprises a top-plan block diagram as configured in accordance with various embodiments of the invention.

Pursuant to these teachings, the ratio of this given distance D to a desired sample interval (as pertains to a final sample set) is approximately an integer that is relatively prime to the number of sampling chains 101 N. As used herein, this reference to "relatively prime" will be understood to refer to two integers that share no common factors. For example, though neither is itself a prime number, the integer 8 is still relatively prime with respect to the integer 15. Also as used in this context, the word "approximately" will be understood to account for the fact that the ratio of real world measured distances is essentially never a true integer. Generally speaking, the tolerance on the spacing between sampling chains may preferably be a small fraction of the final sample pitch. For example, less than ten percent of that pitch may be acceptable for many application settings. Presuming a 10 mm sample pitch (with a 40 mm advance and N=4), this would correspond to a 1 mm tolerance out of a value roughly equal to 1 meter.

This condition can be stated in terms of the ratio of the sampling chain spacing D divided by the final sample pitch P. Here, the advance per sample can be represented as $$A = V \times T$$

where V is the velocity and T is the sample period.

$$V \times T = A = N \times P$$

where N is an integer greater than 1. And $$D/P = I$$

where I is an integer relatively prime to N. This constraint on the integer ratio I ensures that the N samples will be distinct.

As noted, I and N are relatively prime to one another. The applicant has noted that if I were an integer multiple of N, then the N sampling chains 100 can strobe the same locations (albeit at different times) such that not all of the spaces are ultimately filled in. In general, if I and N contain common factors, significant gaps in the sampling data can result.

Figure 4:
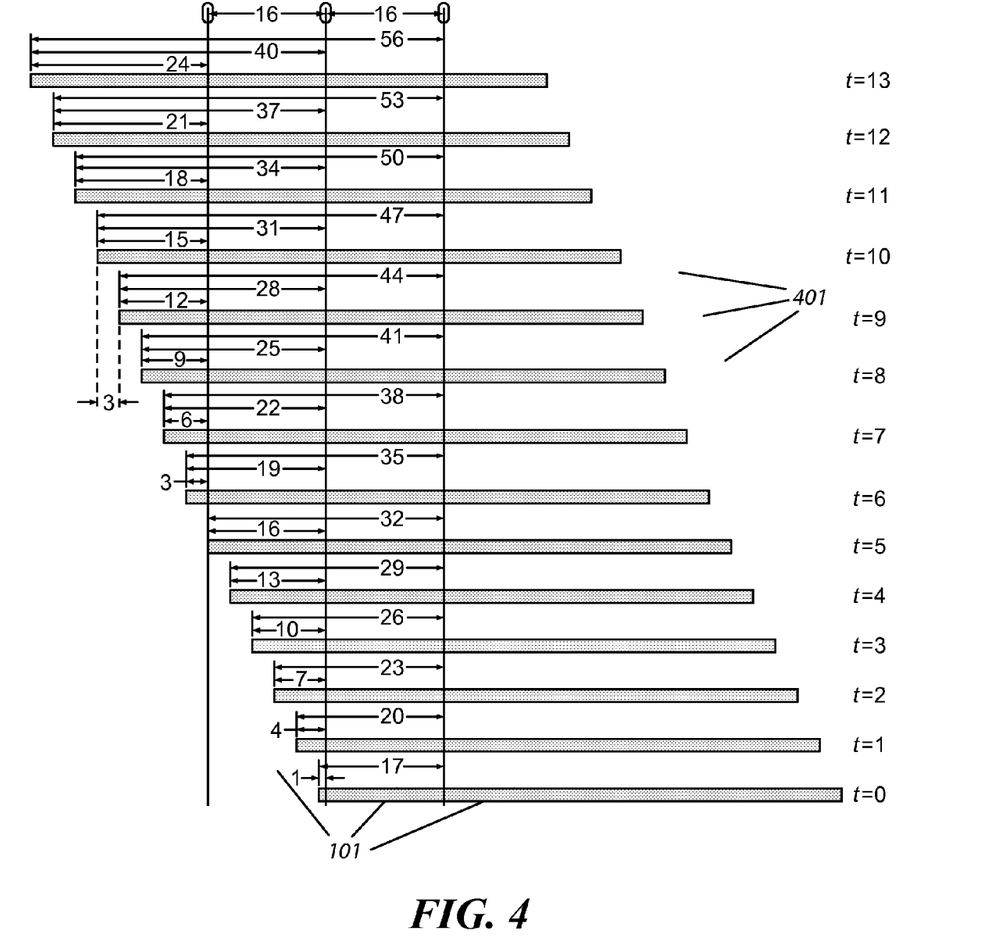
FIG. 4 comprises a top-plan timing diagram as configured in accordance with various embodiments of the invention.

As a simple example in these regards, and referring now momentarily to FIG. 4, there are three sampling chains 101 and hence N=3. I, however, will be much larger, such as 199 (a prime number), to make the spacing D between the sampling chains D=199×(5 mm)=995 mm. FIG. 4 reflects a case where N=3 and I=16 that serves to illustrate one basic concept of these teachings. Those skilled in the art will recognize and understand, of course, that the minimum spacing for any given practical application will be constrained, at least in part, by the physical size of the source itself.

In FIG. 4, the numerical values for distance are given in units of the final sample pitch P. The case illustrated is appropriate for this particular example, since with P=5 mm and I=16, the center-to-center spacing between the sampling chains 101 is only 80 mm. The succession of grey rectangles 401 from bottom to top represents the position of the object (in these examples, the aforementioned train 100) at the times given on the right margin. The three vertical lines represent the centers of the widely-spaced sampling chains 101. The horizontal dimension lines on each rectangle 401 represent the distance from one end of the object to the two or three samples that strobed the object. Those skilled in the art will note that this FIG. depicts 42 of 56 locations; the missing 14 locations would be shown if this figure included more rectangles below the figure (negative time values) and these 14 positions would be sampled only by the right-most of the three sampling chains 101. Similarly, sample positions greater than 56 would be seen for positions with t>13, above those shown in FIG. 4. The latter omissions are made for the sake of simplicity and clarity.

With continued reference to FIG. 4, the described approach will benefit from the use of precise values for the integer ratio I. Since P should be constant in the final image, the applicant has determined that it may therefore be beneficial to control A, the physical advance per sample. This, in turn, will benefit from knowing the (preferably constant) velocity of the object 401.

Referring again to FIG. 2, this process 200 will therefore accommodate the optional step 202 of determining a relative velocity as between the object and the sampling chains 101 (for example, by measuring the speed of an oncoming train 100) along with the optional step 203 of using this relative velocity to determine when to pulse the sampling chains 101 to capture corresponding samples of the object. For an almost constant velocity as monitored by the control system, the actual pulse repetition time T can be adjusted pulse-by-pulse to achieve a constant advance A.

As noted above, these teachings benefit from using a relatively prime pair of integers for the number of chains N and the ratio I. In an illustrative case where I=199, this approach benefits from ensuring that the actual ratio is within a small fraction of this integer. Since I=D/P, this can be controlled by choosing a numerical value of the image pitch P to agree with the physical value of D. For the ratio N, one can adjust the advance A to agree with this chosen value of P. When the velocity V is reasonably constant and can be measured continuously, the exact value of T can be changed from pulse to pulse to keep the product A=V×T constant.

If, however, the velocity varies too much during the process, the required T may violate an allowable range for the source pulsing. In such an extreme case, the ratio I can be set to a different integer, still relatively prime to N, with careful resorting of the resulting data. If, however, the velocity can be maintained constant within, say, a 10% range with a measurement resolution of 0.1%, then the integer I can be kept within about plus-or-minus 0.2 of its nominal integer value 199. As railroad trains typically cannot accelerate or decelerate quickly, this may not present much of an issue in a train-based application setting.

With continued reference to both FIGS. 2 and 4, this process 200 will also accommodate the step 204 of using these sampling chains 101 to capture a complete set of samples in a corresponding chronological order. Those skilled in the art will note, however, that such an approach will not yield a chronologically-acquired sequence of samples that also matches the order in which these samples should be placed in order to represent a contiguous view of the object 401. Accordingly, these samples will need to be sorted to achieve the standard order 1 to 56. This process 200 will therefore also accommodate the step 205 of reordering these samples in other than the chronological order of capture to thereby provide reordered samples that can then be used, in step 206, to provide an image of the object.

Figure 6:
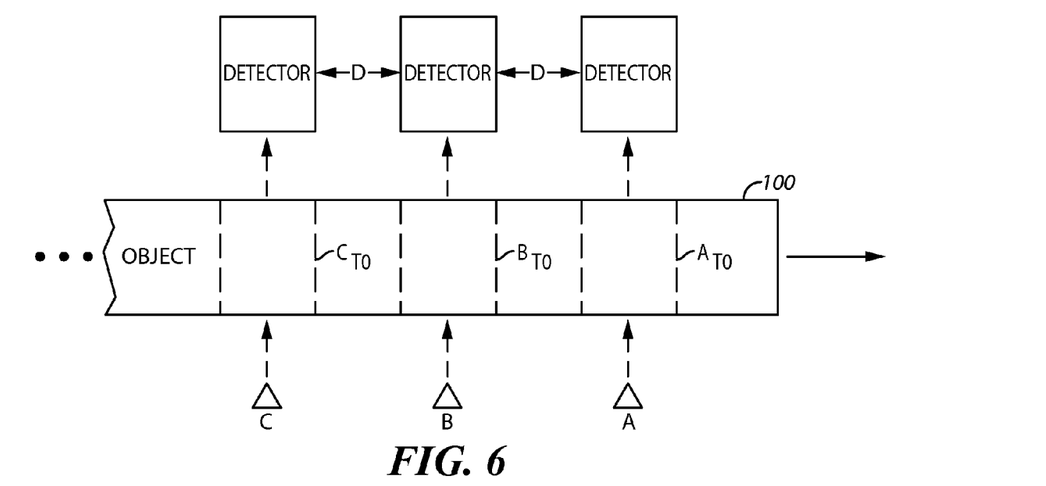
FIG. 6 comprises a top-plan schematic view as configured in accordance with various embodiments of the invention.
Figure 7:
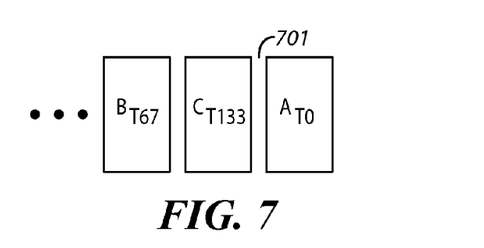
FIG. 7 comprises a schematic representation as configured in accordance with various embodiments of the invention.

To illustrate, and referring momentarily to FIGS. 6 and 7, in a given application setting an object 100 moves through three sampling chains A, B, and C where adjacent sampling chains are equally separated from one another by a distance D. In this example it is presumed that the sources for each sampling chain A, B, and C are simultaneously pulsed. In such a case, for a given pulse at time T0 sampling chain A will capture a sample denoted as $A_{T0}$, sampling chain B will capture a sample denoted as $B_{T0}$, and sampling chain C will capture a sample denoted as $C_{T0}$. These samples will only comprise a small portion of the object 100 and it will require a number of samples by each of the sampling chains to acquire all of the samples that are necessary to image the complete object 100.

As noted above, a chronological sequence of these samples will not correctly represent the object 100. Instead, they must be reordered. As suggested by the illustration provided in FIG. 7, this will likely involve reordering the samples such that samples captured at considerably different times are now adjacent to one another. In the example shown, for instance, a sample denoted by $C_{T133}$ is placed between a first sample denoted by $B_{T67}$ and another sample denoted by $A_{T0}$. It is possible that a small gap (representing, for example, a 1 mm gap) 701 may exist between each such sample. It will be understood that the resultant corresponding image is nevertheless reasonably considered to be "complete."

Those skilled in the art will appreciate that the above-described processes are readily enabled using any of a wide variety of available and/or readily configured platforms, including partially or wholly programmable platforms as are known in the art or dedicated purpose platforms as may be desired for some applications. Referring again to FIG. 3, an illustrative approach to such a platform will now be provided.

In this illustrative example the sampling chains 101 are fixed in place (at least during use; part or all of each sampling chain 101 may, of course, be movable in accord with well-understood prior art practice in these regards) and it is the object 100 that will be moving past the sampling chains 101. The number of sampling chains 101 employed in a given application setting can vary with the needs and/or opportunities as tend to characterize that setting. This is represented here by presenting a first sampling chain 301 through an Nth sampling chain 302 (where N will be understood to comprise an integer greater than 1). For example, N can be at least 3.

By one optional approach, and as illustrated, each of the sampling chains 101 can be communicatively coupled to and at least partially controlled by a control circuit 303. This control circuit 303, for example, can be operably coupled to the sources 102 for each of the sampling chains 101. So configured, the control circuit 303 can be configured to control the pulsed energization of each of the sampling chains 101.

Those skilled in the art will recognize and appreciate that such a control circuit 303 can comprise a fixed-purpose hard-wired platform or can comprise a partially or wholly programmable platform. All of these architectural options are well known and understood in the art and require no further description here.

As noted earlier, these teachings will optionally accommodate detecting the speed of the approaching object 100. By one approach, a velocity measurement component 304 that communicatively couples to the control circuit 303 can support such functionality. Various velocity measurement components are known in the art. Some, for example, are based upon radar mechanisms. As these teachings are not overly sensitive to any particular selection in this regard, for the sake of brevity and the preservation of clarity, further elaboration in this regard will not be presented here. So configured, the control circuit 303 can be apprised of the velocity of the approaching object 100. In such a case the control circuit 303 can be further configured to control the pulsed energization of the sampling chains 101 as a function of the relative velocity between the object 100 and the sampling chains 101 as measured by this velocity measuring component 304.

By one approach, and particularly when the control circuit 303 comprises a partially or wholly programmable platform, a memory 305 can operably couple to the control circuit 303. This can be particularly helpful when the control circuit 303 itself lacks sufficient native memory resources. So configured, this memory 305 can contain computer instructions that, when executed by the control circuit 303, cause the latter to perform one or more of the steps, actions, and/or functions described herein.

A memory 306 can also be communicatively coupled to the detectors 103 of the sampling chains 101. Such a memory 306 can serve, for example, to receive and to store the samples of the object as are captured by the sampling chains 101. Those skilled in the art will recognize, of course, that these two memories 305 and 306 can comprise a same memory or can comprise discrete components as desired.

In the sampling chains 101 described above, each sampling chain 101 has a single source 102 and a single corresponding detector 103 (where the detector 103 comprises a single vertical detector array). These teachings will accommodate other approaches in these regards, however. In particular, the applicant has determined that certain benefits may sometimes be realized by employing two or more detector arrays in the detector 103 of one or more of the sampling chains 101.

To illustrate, the system described above, with only three sampling chains 101, can achieve a 5 mm sample pitch at high velocity if a 1,000 Hz pulse-repetition frequency can be achieved. With, however, a similar velocity (assume 16 m/s for the sake of simplicity) and the same pitch but a pulse period of 2.5 ms (the catalog value of many current linear accelerators), the number of sampling chains 101 would increase beyond three at increased expense. In this case, still using a single detector array per sampling chain 101, the advance per pulse A=(16 m/s)×(2.5 ms)=40 mm, and the ratio N=8 for sample pitch P=5 mm.

Figure 5:
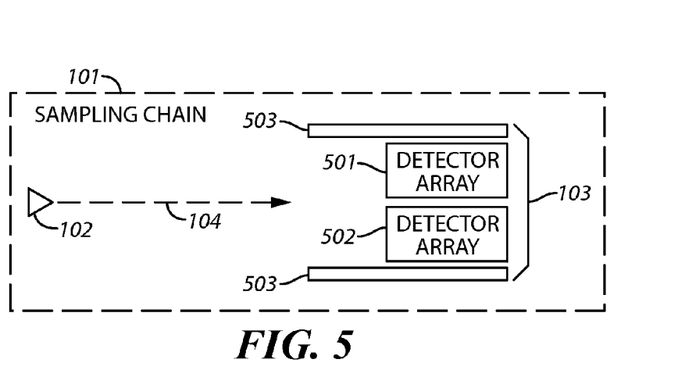
FIG. 5 comprises a top-plan block diagram as configured in accordance with various embodiments of the invention.

This situation can be improved in many application settings by providing additional side-by-side detector arrays for use with a shared source 102. It is relatively easy to mount two detector arrays back-to-back with small spacing between them and irradiate them from one source 102, where the two sampling planes are almost parallel (allowing for some small angular error). FIG. 5 illustrates such an approach. In this illustrative example the detector 103 comprises two side-by-side detector arrays 501 and 502. The space between such detector arrays 501 and 502 can be quite small (on the order, for example, of about 1 mm).

In a given challenging application setting, for example, such an approach would reduce the number of relatively expensive sources from 8 to 4. The spacing between these pairs would be similar to the spacing between the single-detector sampling chains 101 described above, with I=199 for D=1990 mm.

One simple way to think of this approach is that each sample on one two-array sampling chain is a long pixel that can be split into two because of the independent detectors. Without splitting, these long pixels can be arranged like the normal pixels in the single-detector system described earlier to obtain full sampling of the object, and then each pixel is split into two to get full sampling with smaller pixels.

With continued reference to FIG. 5, these teachings will also accommodate disposing side-scatter shielding 503 on either side of each of the sampling chains 101 (and in particular on either side of the detector array(s)). Such shielding can be formed, for example, of lead or tungsten. By one approach, this shielding 503 can extend forwardly of the detector elements a distance sufficient, in a given application setting, to reduce the acceptance of scattered signal that is out of the plane of the sampling chain 101. This might be a length, for example, that is sufficient to reduce the admittance of such scattered signal by 30%, 50%, 75%, 90%, or the like as desired.

EXAMPLE 1

This first example presumes a fast-moving train traveling at 54.0 km/hr (which equates to 15 m/sec and 15,000 mm/sec) and the presence of three equally-spaced sampling chains 101 and the use of a high pulse rate (i.e., PRF=1,000.0 Hz). More particularly, the sampling chains 101 are spaced such that I=199. A first sampling chain 101 can be viewed as being located at 0 mm. Using that as a point of reference, the middle sampling chain 101 is located at 995 mm and the third sampling chain 101 is located at 1990 mm. In this example, the positive locations are along the stationary track with position values increasing in the direction of forward motion. The sampling pitch is 5 mm. The train's advance per sample is therefore 15 mm.

Table 1 shown below presents the relative location of each sample captured by each sampling chain 101 at each sample time. Negative locations denote samples taken at positions in the train sampled before the sample taken at time zero in the chain located at position 0. These negative positions are farther in the direction of motion than positive locations, and positive numbers refer to locations within the train closer to the trailing end of the train. At sample time 0.0 ms, for example, only the sampling chain at location 0 mm captures a non-negative sample. At sample time 133.0 ms, it is the sampling chain at location 1990 mm that captures the next physically adjacent segment of the train at location 5 mm. Similarly, the next physically adjacent segment of the train, at location 10 mm, is captured at sample time 67.0 ms by the sampling chain at location 995 mm. (To ease a review of this table for these particular samples, each of these indicated samples appears within a box.)

Table 1 therefore clearly reveals that the described approach provides for completely sampling the entire train, albeit with samples that are chronologically disordered. The capture pattern, however, is highly predictable and it comprises an essentially trivial task to reorder the captured samples to reconstruct a contiguous image of the train.

TABLE 1

| Sample No. | Sample Time (ms) | 0 | 995 | 1990 |
|---|---|---|---|---|
| | | Strobed sample locations (mm) | | |
| 0 | 0.0 | 0 | −995 | −1990 |
| 1 | 1.0 | 15 | −980 | −1975 |
| 2 | 2.0 | 30 | −965 | −1960 |
| 3 | 3.0 | 45 | −950 | −1945 |
| 4 | 4.0 | 60 | −935 | −1930 |
| 5 | 5.0 | 75 | −920 | −1915 |
| 6 | 6.0 | 90 | −905 | −1900 |
| 7 | 7.0 | 105 | −890 | −1885 |
| 8 | 8.0 | 120 | −875 | −1870 |
| 9 | 9.0 | 135 | −860 | −1855 |
| 10 | 10.0 | 150 | −845 | −1840 |
| 11 | 11.0 | 165 | −830 | −1825 |
| 12 | 12.0 | 180 | −815 | −1810 |
| 13 | 13.0 | 195 | −800 | −1795 |
| 14 | 14.0 | 210 | −785 | −1780 |
| 15 | 15.0 | 225 | −770 | −1765 |
| 16 | 16.0 | 240 | −755 | −1750 |
| 17 | 17.0 | 255 | −740 | −1735 |
| 18 | 18.0 | 270 | −725 | −1720 |
| 19 | 19.0 | 285 | −710 | −1705 |
| 20 | 20.0 | 300 | −695 | −1690 |
| 21 | 21.0 | 315 | −680 | −1675 |
| 22 | 22.0 | 330 | −665 | −1660 |
| 23 | 23.0 | 345 | −650 | −1645 |
| 24 | 24.0 | 360 | −635 | −1630 |
| 25 | 25.0 | 375 | −620 | −1615 |
| 26 | 26.0 | 390 | −605 | −1600 |
| 27 | 27.0 | 405 | −590 | −1585 |
| 28 | 28.0 | 420 | −575 | −1570 |
| 29 | 29.0 | 435 | −560 | −1555 |
| 30 | 30.0 | 450 | −545 | −1540 |
| 31 | 31.0 | 465 | −530 | −1525 |
| 32 | 32.0 | 480 | −515 | −1510 |
| 33 | 33.0 | 495 | −500 | −1495 |
| 34 | 34.0 | 510 | −485 | −1480 |
| 35 | 35.0 | 525 | −470 | −1465 |
| 36 | 36.0 | 540 | −455 | −1450 |
| 37 | 37.0 | 555 | −440 | −1435 |
| 38 | 38.0 | 570 | −425 | −1420 |
| 39 | 39.0 | 585 | −410 | −1405 |
| 40 | 40.0 | 600 | −395 | −1390 |
| 41 | 41.0 | 615 | −380 | −1375 |
| 42 | 42.0 | 630 | −365 | −1360 |
| 43 | 43.0 | 645 | −350 | −1345 |
| 44 | 44.0 | 660 | −335 | −1330 |
| 45 | 45.0 | 675 | −320 | −1315 |
| 46 | 46.0 | 690 | −305 | −1300 |
| 47 | 47.0 | 705 | −290 | −1285 |
| 48 | 48.0 | 720 | −275 | −1270 |
| 49 | 49.0 | 735 | −260 | −1255 |
| 50 | 50.0 | 750 | −245 | −1240 |
| 51 | 51.0 | 765 | −230 | −1225 |
| 52 | 52.0 | 780 | −215 | −1210 |
| 53 | 53.0 | 795 | −200 | −1195 |
| 54 | 54.0 | 810 | −185 | −1180 |
| 55 | 55.0 | 825 | −170 | −1165 |
| 56 | 56.0 | 840 | −155 | −1150 |
| 57 | 57.0 | 855 | −140 | −1135 |
| 58 | 58.0 | 870 | −125 | −1120 |
| 59 | 59.0 | 885 | −110 | −1105 |
| 60 | 60.0 | 900 | −95 | −1090 |
| 61 | 61.0 | 915 | −80 | −1075 |
| 62 | 62.0 | 930 | −65 | −1060 |
| 63 | 63.0 | 945 | −50 | −1045 |
| 64 | 64.0 | 960 | −35 | −1030 |
| 65 | 65.0 | 975 | −20 | −1015 |
| 66 | 66.0 | 990 | −5 | −1000 |
| 67 | 67.0 | 1005 | 10 | −985 |
| 68 | 68.0 | 1020 | 25 | −970 |
| 69 | 69.0 | 1035 | 40 | −955 |
| 70 | 70.0 | 1050 | 55 | −940 |
| 71 | 71.0 | 1065 | 70 | −925 |
| 72 | 72.0 | 1080 | 85 | −910 |
| 73 | 73.0 | 1095 | 100 | −895 |
| 74 | 74.0 | 1110 | 115 | −880 |
| 75 | 75.0 | 1125 | 130 | −865 |
| 76 | 76.0 | 1140 | 145 | −850 |
| 77 | 77.0 | 1155 | 160 | −835 |
| 78 | 78.0 | 1170 | 175 | −820 |
| 79 | 79.0 | 1185 | 190 | −805 |
| 80 | 80.0 | 1200 | 205 | −790 |
| 81 | 81.0 | 1215 | 220 | −775 |
| 82 | 82.0 | 1230 | 235 | −760 |
| 83 | 83.0 | 1245 | 250 | −745 |
| 84 | 84.0 | 1260 | 265 | −730 |
| 85 | 85.0 | 1275 | 280 | −715 |
| 86 | 86.0 | 1290 | 295 | −700 |
| 87 | 87.0 | 1305 | 310 | −685 |
| 88 | 88.0 | 1320 | 325 | −670 |
| 89 | 89.0 | 1335 | 340 | −655 |
| 90 | 90.0 | 1350 | 355 | −640 |
| 91 | 91.0 | 1365 | 370 | −625 |
| 92 | 92.0 | 1380 | 385 | −610 |
| 93 | 93.0 | 1395 | 400 | −595 |
| 94 | 94.0 | 1410 | 415 | −580 |
| 95 | 95.0 | 1425 | 430 | −565 |
| 96 | 96.0 | 1440 | 445 | −550 |
| 97 | 97.0 | 1455 | 460 | −535 |
| 98 | 98.0 | 1470 | 475 | −520 |
| 99 | 99.0 | 1485 | 490 | −505 |
| 100 | 100.0 | 1500 | 505 | −490 |
| 101 | 101.0 | 1515 | 520 | −475 |
| 102 | 102.0 | 1530 | 535 | −460 |
| 103 | 103.0 | 1545 | 550 | −445 |
| 104 | 104.0 | 1560 | 565 | −430 |
| 105 | 105.0 | 1575 | 580 | −415 |
| 106 | 106.0 | 1590 | 595 | −400 |
| 107 | 107.0 | 1605 | 610 | −385 |

TABLE 1-continued

| Sample No. | Sample Time (ms) | Sampling chain locations (mm) | | |
|---|---|---|---|---|
| | | 0 | 995 | 1990 |
| | | Strobed sample locations (mm) | | |
| 108 | 108.0 | 1620 | 625 | −370 |
| 109 | 109.0 | 1635 | 640 | −355 |
| 110 | 110.0 | 1650 | 655 | −340 |
| 111 | 111.0 | 1665 | 670 | −325 |
| 112 | 112.0 | 1680 | 685 | −310 |
| 113 | 113.0 | 1695 | 700 | −295 |
| 114 | 114.0 | 1710 | 715 | −280 |
| 115 | 115.0 | 1725 | 730 | −265 |
| 116 | 116.0 | 1740 | 745 | −250 |
| 117 | 117.0 | 1755 | 760 | −235 |
| 118 | 118.0 | 1770 | 775 | −220 |
| 119 | 119.0 | 1785 | 790 | −205 |
| 120 | 120.0 | 1800 | 805 | −190 |
| 121 | 121.0 | 1815 | 820 | −175 |
| 122 | 122.0 | 1830 | 835 | −160 |
| 123 | 123.0 | 1845 | 850 | −145 |
| 124 | 124.0 | 1860 | 865 | −130 |
| 125 | 125.0 | 1875 | 880 | −115 |
| 126 | 126.0 | 1890 | 895 | −100 |
| 127 | 127.0 | 1905 | 910 | −85 |
| 128 | 128.0 | 1920 | 925 | −70 |
| 129 | 129.0 | 1935 | 940 | −55 |
| 130 | 130.0 | 1950 | 955 | −40 |
| 131 | 131.0 | 1965 | 970 | −25 |
| 132 | 132.0 | 1980 | 985 | −10 |
| 133 | 133.0 | 1995 | 1000 | 5 |
| 134 | 134.0 | 2010 | 1015 | 20 |
| 135 | 135.0 | 2025 | 1030 | 35 |
| 136 | 136.0 | 2040 | 1045 | 50 |
| 137 | 137.0 | 2055 | 1060 | 65 |
| 138 | 138.0 | 2070 | 1075 | 80 |
| 139 | 139.0 | 2085 | 1090 | 95 |
| 140 | 140.0 | 2100 | 1105 | 110 |
| 141 | 141.0 | 2115 | 1120 | 125 |
| 142 | 142.0 | 2130 | 1135 | 140 |
| 143 | 143.0 | 2145 | 1150 | 155 |
| 144 | 144.0 | 2160 | 1165 | 170 |
| 145 | 145.0 | 2175 | 1180 | 185 |
| 146 | 146.0 | 2190 | 1195 | 200 |
| 147 | 147.0 | 2205 | 1210 | 215 |
| 148 | 148.0 | 2220 | 1225 | 230 |
| 149 | 149.0 | 2235 | 1240 | 245 |
| 150 | 150.0 | 2250 | 1255 | 260 |
| 151 | 151.0 | 2265 | 1270 | 275 |
| 152 | 152.0 | 2280 | 1285 | 290 |
| 153 | 153.0 | 2295 | 1300 | 305 |
| 154 | 154.0 | 2310 | 1315 | 320 |
| 155 | 155.0 | 2325 | 1330 | 335 |
| 156 | 156.0 | 2340 | 1345 | 350 |
| 157 | 157.0 | 2355 | 1360 | 365 |
| 158 | 158.0 | 2370 | 1375 | 380 |
| 159 | 159.0 | 2385 | 1390 | 395 |
| 160 | 160.0 | 2400 | 1405 | 410 |
| 161 | 161.0 | 2415 | 1420 | 425 |
| 162 | 162.0 | 2430 | 1435 | 440 |
| 163 | 163.0 | 2445 | 1450 | 455 |
| 164 | 164.0 | 2460 | 1465 | 470 |
| 165 | 165.0 | 2475 | 1480 | 485 |
| 166 | 166.0 | 2490 | 1495 | 500 |
| 167 | 167.0 | 2505 | 1510 | 515 |
| 168 | 168.0 | 2520 | 1525 | 530 |
| 169 | 169.0 | 2535 | 1540 | 545 |
| 170 | 170.0 | 2550 | 1555 | 560 |
| 171 | 171.0 | 2565 | 1570 | 575 |
| 172 | 172.0 | 2580 | 1585 | 590 |
| 173 | 173.0 | 2595 | 1600 | 605 |
| 174 | 174.0 | 2610 | 1615 | 620 |
| 175 | 175.0 | 2625 | 1630 | 635 |
| 176 | 176.0 | 2640 | 1645 | 650 |
| 177 | 177.0 | 2655 | 1660 | 665 |
| 178 | 178.0 | 2670 | 1675 | 680 |
| 179 | 179.0 | 2685 | 1690 | 695 |
| 180 | 180.0 | 2700 | 1705 | 710 |
| 181 | 181.0 | 2715 | 1720 | 725 |
| 182 | 182.0 | 2730 | 1735 | 740 |
| 183 | 183.0 | 2745 | 1750 | 755 |
| 184 | 184.0 | 2760 | 1765 | 770 |
| 185 | 185.0 | 2775 | 1780 | 785 |
| 186 | 186.0 | 2790 | 1795 | 800 |
| 187 | 187.0 | 2805 | 1810 | 815 |
| 188 | 188.0 | 2820 | 1825 | 830 |
| 189 | 189.0 | 2835 | 1840 | 845 |
| 190 | 190.0 | 2850 | 1855 | 860 |
| 191 | 191.0 | 2865 | 1870 | 875 |
| 192 | 192.0 | 2880 | 1885 | 890 |
| 193 | 193.0 | 2895 | 1900 | 905 |
| 194 | 194.0 | 2910 | 1915 | 920 |
| 195 | 195.0 | 2925 | 1930 | 935 |
| 196 | 196.0 | 2940 | 1945 | 950 |
| 197 | 197.0 | 2955 | 1960 | 965 |
| 198 | 198.0 | 2970 | 1975 | 980 |
| 199 | 199.0 | 2985 | 1990 | 995 |
| 200 | 200.0 | 3000 | 2005 | 1010 |
| 201 | 201.0 | 3015 | 2020 | 1025 |
| 202 | 202.0 | 3030 | 2035 | 1040 |
| 203 | 203.0 | 3045 | 2050 | 1055 |
| 204 | 204.0 | 3060 | 2065 | 1070 |
| 205 | 205.0 | 3075 | 2080 | 1085 |
| 206 | 206.0 | 3090 | 2095 | 1100 |
| 207 | 207.0 | 3105 | 2110 | 1115 |
| 208 | 208.0 | 3120 | 2125 | 1130 |
| 209 | 209.0 | 3135 | 2140 | 1145 |
| 210 | 210.0 | 3150 | 2155 | 1160 |
| 211 | 211.0 | 3165 | 2170 | 1175 |
| 212 | 212.0 | 3180 | 2185 | 1190 |
| 213 | 213.0 | 3195 | 2200 | 1205 |
| 214 | 214.0 | 3210 | 2215 | 1220 |
| 215 | 215.0 | 3225 | 2230 | 1235 |
| 216 | 216.0 | 3240 | 2245 | 1250 |
| 217 | 217.0 | 3255 | 2260 | 1265 |
| 218 | 218.0 | 3270 | 2275 | 1280 |
| 219 | 219.0 | 3285 | 2290 | 1295 |
| 220 | 220.0 | 3300 | 2305 | 1310 |
| 221 | 221.0 | 3315 | 2320 | 1325 |
| 222 | 222.0 | 3330 | 2335 | 1340 |
| 223 | 223.0 | 3345 | 2350 | 1355 |
| 224 | 224.0 | 3360 | 2365 | 1370 |
| 225 | 225.0 | 3375 | 2380 | 1385 |
| 226 | 226.0 | 3390 | 2395 | 1400 |
| 227 | 227.0 | 3405 | 2410 | 1415 |
| 228 | 228.0 | 3420 | 2425 | 1430 |
| 229 | 229.0 | 3435 | 2440 | 1445 |
| 230 | 230.0 | 3450 | 2455 | 1460 |
| 231 | 231.0 | 3465 | 2470 | 1475 |
| 232 | 232.0 | 3480 | 2485 | 1490 |
| 233 | 233.0 | 3495 | 2500 | 1505 |
| 234 | 234.0 | 3510 | 2515 | 1520 |
| 235 | 235.0 | 3525 | 2530 | 1535 |
| 236 | 236.0 | 3540 | 2545 | 1550 |
| 237 | 237.0 | 3555 | 2560 | 1565 |
| 238 | 238.0 | 3570 | 2575 | 1580 |
| 239 | 239.0 | 3585 | 2590 | 1595 |
| 240 | 240.0 | 3600 | 2605 | 1610 |
| 241 | 241.0 | 3615 | 2620 | 1625 |
| 242 | 242.0 | 3630 | 2635 | 1640 |
| 243 | 243.0 | 3645 | 2650 | 1655 |
| 244 | 244.0 | 3660 | 2665 | 1670 |
| 245 | 245.0 | 3675 | 2680 | 1685 |
| 246 | 246.0 | 3690 | 2695 | 1700 |
| 247 | 247.0 | 3705 | 2710 | 1715 |
| 248 | 248.0 | 3720 | 2725 | 1730 |
| 249 | 249.0 | 3735 | 2740 | 1745 |
| 250 | 250.0 | 3750 | 2755 | 1760 |
| 251 | 251.0 | 3765 | 2770 | 1775 |
| 252 | 252.0 | 3780 | 2785 | 1790 |
| 253 | 253.0 | 3795 | 2800 | 1805 |
| 254 | 254.0 | 3810 | 2815 | 1820 |
| 255 | 255.0 | 3825 | 2830 | 1835 |
| 256 | 256.0 | 3840 | 2845 | 1850 |

TABLE 1-continued

| Sample No. | Sample Time (ms) | Sampling chain locations (mm) | | |
|---|---|---|---|---|
| | | 0 | 995 | 1990 |
| | | Strobed sample locations (mm) | | |
| 257 | 257.0 | 3855 | 2860 | 1865 |
| 258 | 258.0 | 3870 | 2875 | 1880 |
| 259 | 259.0 | 3885 | 2890 | 1895 |
| 260 | 260.0 | 3900 | 2905 | 1910 |
| 261 | 261.0 | 3915 | 2920 | 1925 |
| 262 | 262.0 | 3930 | 2935 | 1940 |
| 263 | 263.0 | 3945 | 2950 | 1955 |
| 264 | 264.0 | 3960 | 2965 | 1970 |
| 265 | 265.0 | 3975 | 2980 | 1985 |
| 266 | 266.0 | 3990 | 2995 | 2000 |
| 267 | 267.0 | 4005 | 3010 | 2015 |
| 268 | 268.0 | 4020 | 3025 | 2030 |
| 269 | 269.0 | 4035 | 3040 | 2045 |
| 270 | 270.0 | 4050 | 3055 | 2060 |
| 271 | 271.0 | 4065 | 3070 | 2075 |
| 272 | 272.0 | 4080 | 3085 | 2090 |
| 273 | 273.0 | 4095 | 3100 | 2105 |
| 274 | 274.0 | 4110 | 3115 | 2120 |
| 275 | 275.0 | 4125 | 3130 | 2135 |
| 276 | 276.0 | 4140 | 3145 | 2150 |
| 277 | 277.0 | 4155 | 3160 | 2165 |
| 278 | 278.0 | 4170 | 3175 | 2180 |
| 279 | 279.0 | 4185 | 3190 | 2195 |
| 280 | 280.0 | 4200 | 3205 | 2210 |
| 281 | 281.0 | 4215 | 3220 | 2225 |
| 282 | 282.0 | 4230 | 3235 | 2240 |
| 283 | 283.0 | 4245 | 3250 | 2255 |
| 284 | 284.0 | 4260 | 3265 | 2270 |
| 285 | 285.0 | 4275 | 3280 | 2285 |
| 286 | 286.0 | 4290 | 3295 | 2300 |
| 287 | 287.0 | 4305 | 3310 | 2315 |
| 288 | 288.0 | 4320 | 3325 | 2330 |
| 289 | 289.0 | 4335 | 3340 | 2345 |
| 290 | 290.0 | 4350 | 3355 | 2360 |
| 291 | 291.0 | 4365 | 3370 | 2375 |
| 292 | 292.0 | 4380 | 3385 | 2390 |
| 293 | 293.0 | 4395 | 3400 | 2405 |
| 294 | 294.0 | 4410 | 3415 | 2420 |
| 295 | 295.0 | 4425 | 3430 | 2435 |
| 296 | 296.0 | 4440 | 3445 | 2450 |
| 297 | 297.0 | 4455 | 3460 | 2465 |
| 298 | 298.0 | 4470 | 3475 | 2480 |
| 299 | 299.0 | 4485 | 3490 | 2495 |
| 300 | 300.0 | 4500 | 3505 | 2510 |

EXAMPLE 2

This second example presumes a fast-moving train traveling at 57.6 km/hr (which equates to 16 m/sec and 16,000 mm/sec) and the presence of four equally-spaced sampling chains 101 (each having two closely-spaced detector arrays as described above) and the use of a lower pulse rate (i.e., PRF=400.0 Hz). The sampling chains 101 are again spaced such that I=199. A first sampling chain 101 can be viewed as being located at 0 mm. Again using that as a point of reference, the second sampling chain 101 is located at 1990 mm, the third sampling chain 101 is located at 3980 mm, and the fourth sampling chain 101 is located at 5970 mm. The higher-numbered sampling chains are farther along the stationary track in the direction of motion in this example. The sampling pitch is now 10 mm with each of the paired arrays capturing 5 mm of that 10 mm spread. The train's advance per sample is therefore 40 mm.

Table 1 again demonstrates that the described approach provides for completely sampling the entire train, albeit with samples that are again chronologically disordered. Again, however, the capture pattern is highly predictable and permits ready reordering as desired. (And again, the first few samples that would be rearranged to correspond to the object itself each appears within a box to facilitate their ready identification by the reader.)

TABLE 2

| Sample No. | Sample Time (ms) | Sampling chain locations (mm) | | | |
|---|---|---|---|---|---|
| | | 0 | 1990 | 3980 | 5970 |
| | | Strobed sample locations (mm) | | | |
| 0 | 0.0 | 0 | −1990 | −3980 | −5970 |
| 1 | 2.5 | 40 | −1950 | −3940 | −5930 |
| 2 | 5.0 | 80 | −1910 | −3900 | −5890 |
| 3 | 7.5 | 120 | −1870 | −3860 | −5850 |
| 4 | 10.0 | 160 | −1830 | −3820 | −5810 |
| 5 | 12.5 | 200 | −1790 | −3780 | −5770 |
| 6 | 15.0 | 240 | −1750 | −3740 | −5730 |
| 7 | 17.5 | 280 | −1710 | −3700 | −5690 |
| 8 | 20.0 | 320 | −1670 | −3660 | −5650 |
| 9 | 22.5 | 360 | −1630 | −3620 | −5610 |
| 10 | 25.0 | 400 | −1590 | −3580 | −5570 |
| 11 | 27.5 | 440 | −1550 | −3540 | −5530 |
| 12 | 30.0 | 480 | −1510 | −3500 | −5490 |
| 13 | 32.5 | 520 | −1470 | −3460 | −5450 |
| 14 | 35.0 | 560 | −1430 | −3420 | −5410 |
| 15 | 37.5 | 600 | −1390 | −3380 | −5370 |
| 16 | 40.0 | 640 | −1350 | −3340 | −5330 |
| 17 | 42.5 | 680 | −1310 | −3300 | −5290 |
| 18 | 45.0 | 720 | −1270 | −3260 | −5250 |
| 19 | 47.5 | 760 | −1230 | −3220 | −5210 |
| 20 | 50.0 | 800 | −1190 | −3180 | −5170 |
| 21 | 52.5 | 840 | −1150 | −3140 | −5130 |
| 22 | 55.0 | 880 | −1110 | −3100 | −5090 |
| 23 | 57.5 | 920 | −1070 | −3060 | −5050 |
| 24 | 60.0 | 960 | −1030 | −3020 | −5010 |
| 25 | 62.5 | 1000 | −990 | −2980 | −4970 |
| 26 | 65.0 | 1040 | −950 | −2940 | −4930 |
| 27 | 67.5 | 1080 | −910 | −2900 | −4890 |
| 28 | 70.0 | 1120 | −870 | −2860 | −4850 |
| 29 | 72.5 | 1160 | −830 | −2820 | −4810 |
| 30 | 75.0 | 1200 | −790 | −2780 | −4770 |
| 31 | 77.5 | 1240 | −750 | −2740 | −4730 |
| 32 | 80.0 | 1280 | −710 | −2700 | −4690 |
| 33 | 82.5 | 1320 | −670 | −2660 | −4650 |
| 34 | 85.0 | 1360 | −630 | −2620 | −4610 |
| 35 | 87.5 | 1400 | −590 | −2580 | −4570 |
| 36 | 90.0 | 1440 | −550 | −2540 | −4530 |
| 37 | 92.5 | 1480 | −510 | −2500 | −4490 |
| 38 | 95.0 | 1520 | −470 | −2460 | −4450 |
| 39 | 97.5 | 1560 | −430 | −2420 | −4410 |
| 40 | 100.0 | 1600 | −390 | −2380 | −4370 |
| 41 | 102.5 | 1640 | −350 | −2340 | −4330 |
| 42 | 105.0 | 1680 | −310 | −2300 | −4290 |
| 43 | 107.5 | 1720 | −270 | −2260 | −4250 |
| 44 | 110.0 | 1760 | −230 | −2220 | −4210 |
| 45 | 112.5 | 1800 | −190 | −2180 | −4170 |
| 46 | 115.0 | 1840 | −150 | −2140 | −4130 |
| 47 | 117.5 | 1880 | −110 | −2100 | −4090 |
| 48 | 120.0 | 1920 | −70 | −2060 | −4050 |
| 49 | 122.5 | 1960 | −30 | −2020 | −4010 |
| 50 | 125.0 | 2000 | 10 | −1980 | −3970 |
| 51 | 127.5 | 2040 | 50 | −1940 | −3930 |
| 52 | 130.0 | 2080 | 90 | −1900 | −3890 |
| 53 | 132.5 | 2120 | 130 | −1860 | −3850 |
| 54 | 135.0 | 2160 | 170 | −1820 | −3810 |
| 55 | 137.5 | 2200 | 210 | −1780 | −3770 |
| 56 | 140.0 | 2240 | 250 | −1740 | −3730 |
| 57 | 142.5 | 2280 | 290 | −1700 | −3690 |
| 58 | 145.0 | 2320 | 330 | −1660 | −3650 |
| 59 | 147.5 | 2360 | 370 | −1620 | −3610 |
| 60 | 150.0 | 2400 | 410 | −1580 | −3570 |
| 61 | 152.5 | 2440 | 450 | −1540 | −3530 |
| 62 | 155.0 | 2480 | 490 | −1500 | −3490 |
| 63 | 157.5 | 2520 | 530 | −1460 | −3450 |
| 64 | 160.0 | 2560 | 570 | −1420 | −3410 |
| 65 | 162.5 | 2600 | 610 | −1380 | −3370 |
| 66 | 165.0 | 2640 | 650 | −1340 | −3330 |
| 67 | 167.5 | 2680 | 690 | −1300 | −3290 |

TABLE 2-continued

| Sample No. | Sample Time (ms) | 0 | 1990 | 3980 | 5970 |
|---|---|---|---|---|---|
| | | Strobed sample locations (mm) | | | |
| 68 | 170.0 | 2720 | 730 | −1260 | −3250 |
| 69 | 172.5 | 2760 | 770 | −1220 | −3210 |
| 70 | 175.0 | 2800 | 810 | −1180 | −3170 |
| 71 | 177.5 | 2840 | 850 | −1140 | −3130 |
| 72 | 180.0 | 2880 | 890 | −1100 | −3090 |
| 73 | 182.5 | 2920 | 930 | −1060 | −3050 |
| 74 | 185.0 | 2960 | 970 | −1020 | −3010 |
| 75 | 187.5 | 3000 | 1010 | −980 | −2970 |
| 76 | 190.0 | 3040 | 1050 | −940 | −2930 |
| 77 | 192.5 | 3080 | 1090 | −900 | −2890 |
| 78 | 195.0 | 3120 | 1130 | −860 | −2850 |
| 79 | 197.5 | 3160 | 1170 | −820 | −2810 |
| 80 | 200.0 | 3200 | 1210 | −780 | −2770 |
| 81 | 202.5 | 3240 | 1250 | −740 | −2730 |
| 82 | 205.0 | 3280 | 1290 | −700 | −2690 |
| 83 | 207.5 | 3320 | 1330 | −660 | −2650 |
| 84 | 210.0 | 3360 | 1370 | −620 | −2610 |
| 85 | 212.5 | 3400 | 1410 | −580 | −2570 |
| 86 | 215.0 | 3440 | 1450 | −540 | −2530 |
| 87 | 217.5 | 3480 | 1490 | −500 | −2490 |
| 88 | 220.0 | 3520 | 1530 | −460 | −2450 |
| 89 | 222.5 | 3560 | 1570 | −420 | −2410 |
| 90 | 225.0 | 3600 | 1610 | −380 | −2370 |
| 91 | 227.5 | 3640 | 1650 | −340 | −2330 |
| 92 | 230.0 | 3680 | 1690 | −300 | −2290 |
| 93 | 232.5 | 3720 | 1730 | −260 | −2250 |
| 94 | 235.0 | 3760 | 1770 | −220 | −2210 |
| 95 | 237.5 | 3800 | 1810 | −180 | −2170 |
| 96 | 240.0 | 3840 | 1850 | −140 | −2130 |
| 97 | 242.5 | 3880 | 1890 | −100 | −2090 |
| 98 | 245.0 | 3920 | 1930 | −60 | −2050 |
| 99 | 247.5 | 3960 | 1970 | −20 | −2010 |
| 100 | 250.0 | 4000 | 2010 | 20 | −1970 |
| 101 | 252.5 | 4040 | 2050 | 60 | −1930 |
| 102 | 255.0 | 4080 | 2090 | 100 | −1890 |
| 103 | 257.5 | 4120 | 2130 | 140 | −1850 |
| 104 | 260.0 | 4160 | 2170 | 180 | −1810 |
| 105 | 262.5 | 4200 | 2210 | 220 | −1770 |
| 106 | 265.0 | 4240 | 2250 | 260 | −1730 |
| 107 | 267.5 | 4280 | 2290 | 300 | −1690 |
| 108 | 270.0 | 4320 | 2330 | 340 | −1650 |
| 109 | 272.5 | 4360 | 2370 | 380 | −1610 |
| 110 | 275.0 | 4400 | 2410 | 420 | −1570 |
| 111 | 277.5 | 4440 | 2450 | 460 | −1530 |
| 112 | 280.0 | 4480 | 2490 | 500 | −1490 |
| 113 | 282.5 | 4520 | 2530 | 540 | −1450 |
| 114 | 285.0 | 4560 | 2570 | 580 | −1410 |
| 115 | 287.5 | 4600 | 2610 | 620 | −1370 |
| 116 | 290.0 | 4640 | 2650 | 660 | −1330 |
| 117 | 292.5 | 4680 | 2690 | 700 | −1290 |
| 118 | 295.0 | 4720 | 2730 | 740 | −1250 |
| 119 | 297.5 | 4760 | 2770 | 780 | −1210 |
| 120 | 300.0 | 4800 | 2810 | 820 | −1170 |
| 121 | 302.5 | 4840 | 2850 | 860 | −1130 |
| 122 | 305.0 | 4880 | 2890 | 900 | −1090 |
| 123 | 307.5 | 4920 | 2930 | 940 | −1050 |
| 124 | 310.0 | 4960 | 2970 | 980 | −1010 |
| 125 | 312.5 | 5000 | 3010 | 1020 | −970 |
| 126 | 315.0 | 5040 | 3050 | 1060 | −930 |
| 127 | 317.5 | 5080 | 3090 | 1100 | −890 |
| 128 | 320.0 | 5120 | 3130 | 1140 | −850 |
| 129 | 322.5 | 5160 | 3170 | 1180 | −810 |
| 130 | 325.0 | 5200 | 3210 | 1220 | −770 |
| 131 | 327.5 | 5240 | 3250 | 1260 | −730 |
| 132 | 330.0 | 5280 | 3290 | 1300 | −690 |
| 133 | 332.5 | 5320 | 3330 | 1340 | −650 |
| 134 | 335.0 | 5360 | 3370 | 1380 | −610 |
| 135 | 337.5 | 5400 | 3410 | 1420 | −570 |
| 136 | 340.0 | 5440 | 3450 | 1460 | −530 |
| 137 | 342.5 | 5480 | 3490 | 1500 | −490 |
| 138 | 345.0 | 5520 | 3530 | 1540 | −450 |
| 139 | 347.5 | 5560 | 3570 | 1580 | −410 |
| 140 | 350.0 | 5600 | 3610 | 1620 | −370 |
| 141 | 352.5 | 5640 | 3650 | 1660 | −330 |
| 142 | 355.0 | 5680 | 3690 | 1700 | −290 |
| 143 | 357.5 | 5720 | 3730 | 1740 | −250 |
| 144 | 360.0 | 5760 | 3770 | 1780 | −210 |
| 145 | 362.5 | 5800 | 3810 | 1820 | −170 |
| 146 | 365.0 | 5840 | 3850 | 1860 | −130 |
| 147 | 367.5 | 5880 | 3890 | 1900 | −90 |
| 148 | 370.0 | 5920 | 3930 | 1940 | −50 |
| 149 | 372.5 | 5960 | 3970 | 1980 | −10 |
| 150 | 375.0 | 6000 | 4010 | 2020 | 30 |
| 151 | 377.5 | 6040 | 4050 | 2060 | 70 |
| 152 | 380.0 | 6080 | 4090 | 2100 | 110 |
| 153 | 382.5 | 6120 | 4130 | 2140 | 150 |
| 154 | 385.0 | 6160 | 4170 | 2180 | 190 |
| 155 | 387.5 | 6200 | 4210 | 2220 | 230 |
| 156 | 390.0 | 6240 | 4250 | 2260 | 270 |
| 157 | 392.5 | 6280 | 4290 | 2300 | 310 |
| 158 | 395.0 | 6320 | 4330 | 2340 | 350 |
| 159 | 397.5 | 6360 | 4370 | 2380 | 390 |
| 160 | 400.0 | 6400 | 4410 | 2420 | 430 |
| 161 | 402.5 | 6440 | 4450 | 2460 | 470 |
| 162 | 405.0 | 6480 | 4490 | 2500 | 510 |
| 163 | 407.5 | 6520 | 4530 | 2540 | 550 |
| 164 | 410.0 | 6560 | 4570 | 2580 | 590 |
| 165 | 412.5 | 6600 | 4610 | 2620 | 630 |
| 166 | 415.0 | 6640 | 4650 | 2660 | 670 |
| 167 | 417.5 | 6680 | 4690 | 2700 | 710 |
| 168 | 420.0 | 6720 | 4730 | 2740 | 750 |
| 169 | 422.5 | 6760 | 4770 | 2780 | 790 |
| 170 | 425.0 | 6800 | 4810 | 2820 | 830 |
| 171 | 427.5 | 6840 | 4850 | 2860 | 870 |
| 172 | 430.0 | 6880 | 4890 | 2900 | 910 |
| 173 | 432.5 | 6920 | 4930 | 2940 | 950 |
| 174 | 435.0 | 6960 | 4970 | 2980 | 990 |
| 175 | 437.5 | 7000 | 5010 | 3020 | 1030 |
| 176 | 440.0 | 7040 | 5050 | 3060 | 1070 |
| 177 | 442.5 | 7080 | 5090 | 3100 | 1110 |
| 178 | 445.0 | 7120 | 5130 | 3140 | 1150 |
| 179 | 447.5 | 7160 | 5170 | 3180 | 1190 |
| 180 | 450.0 | 7200 | 5210 | 3220 | 1230 |
| 181 | 452.5 | 7240 | 5250 | 3260 | 1270 |
| 182 | 455.0 | 7280 | 5290 | 3300 | 1310 |
| 183 | 457.5 | 7320 | 5330 | 3340 | 1350 |
| 184 | 460.0 | 7360 | 5370 | 3380 | 1390 |
| 185 | 462.5 | 7400 | 5410 | 3420 | 1430 |
| 186 | 465.0 | 7440 | 5450 | 3460 | 1470 |
| 187 | 467.5 | 7480 | 5490 | 3500 | 1510 |
| 188 | 470.0 | 7520 | 5530 | 3540 | 1550 |
| 189 | 472.5 | 7560 | 5570 | 3580 | 1590 |
| 190 | 475.0 | 7600 | 5610 | 3620 | 1630 |
| 191 | 477.5 | 7640 | 5650 | 3660 | 1670 |
| 192 | 480.0 | 7680 | 5690 | 3700 | 1710 |
| 193 | 482.5 | 7720 | 5730 | 3740 | 1750 |
| 194 | 485.0 | 7760 | 5770 | 3780 | 1790 |
| 195 | 487.5 | 7800 | 5810 | 3820 | 1830 |
| 196 | 490.0 | 7840 | 5850 | 3860 | 1870 |
| 197 | 492.5 | 7880 | 5890 | 3900 | 1910 |
| 198 | 495.0 | 7920 | 5930 | 3940 | 1950 |
| 199 | 497.5 | 7960 | 5970 | 3980 | 1990 |
| 200 | 500.0 | 8000 | 6010 | 4020 | 2030 |
| 201 | 502.5 | 8040 | 6050 | 4060 | 2070 |
| 202 | 505.0 | 8080 | 6090 | 4100 | 2110 |
| 203 | 507.5 | 8120 | 6130 | 4140 | 2150 |
| 204 | 510.0 | 8160 | 6170 | 4180 | 2190 |
| 205 | 512.5 | 8200 | 6210 | 4220 | 2230 |
| 206 | 515.0 | 8240 | 6250 | 4260 | 2270 |
| 207 | 517.5 | 8280 | 6290 | 4300 | 2310 |
| 208 | 520.0 | 8320 | 6330 | 4340 | 2350 |
| 209 | 522.5 | 8360 | 6370 | 4380 | 2390 |
| 210 | 525.0 | 8400 | 6410 | 4420 | 2430 |
| 211 | 527.5 | 8440 | 6450 | 4460 | 2470 |
| 212 | 530.0 | 8480 | 6490 | 4500 | 2510 |
| 213 | 532.5 | 8520 | 6530 | 4540 | 2550 |
| 214 | 535.0 | 8560 | 6570 | 4580 | 2590 |
| 215 | 537.5 | 8600 | 6610 | 4620 | 2630 |

TABLE 2-continued

| Sample No. | Sample Time (ms) | Sampling chain locations (mm) | | | |
|---|---|---|---|---|---|
| | | 0 | 1990 | 3980 | 5970 |
| | | Strobed sample locations (mm) | | | |
| 216 | 540.0 | 8640 | 6650 | 4660 | 2670 |
| 217 | 542.5 | 8680 | 6690 | 4700 | 2710 |
| 218 | 545.0 | 8720 | 6730 | 4740 | 2750 |
| 219 | 547.5 | 8760 | 6770 | 4780 | 2790 |
| 220 | 550.0 | 8800 | 6810 | 4820 | 2830 |
| 221 | 552.5 | 8840 | 6850 | 4860 | 2870 |
| 222 | 555.0 | 8880 | 6890 | 4900 | 2910 |
| 223 | 557.5 | 8920 | 6930 | 4940 | 2950 |
| 224 | 560.0 | 8960 | 6970 | 4980 | 2990 |
| 225 | 562.5 | 9000 | 7010 | 5020 | 3030 |
| 226 | 565.0 | 9040 | 7050 | 5060 | 3070 |
| 227 | 567.5 | 9080 | 7090 | 5100 | 3110 |
| 228 | 570.0 | 9120 | 7130 | 5140 | 3150 |
| 229 | 572.5 | 9160 | 7170 | 5180 | 3190 |
| 230 | 575.0 | 9200 | 7210 | 5220 | 3230 |
| 231 | 577.5 | 9240 | 7250 | 5260 | 3270 |
| 232 | 580.0 | 9280 | 7290 | 5300 | 3310 |
| 233 | 582.5 | 9320 | 7330 | 5340 | 3350 |
| 234 | 585.0 | 9360 | 7370 | 5380 | 3390 |
| 235 | 587.5 | 9400 | 7410 | 5420 | 3430 |
| 236 | 590.0 | 9440 | 7450 | 5460 | 3470 |
| 237 | 592.5 | 9480 | 7490 | 5500 | 3510 |
| 238 | 595.0 | 9520 | 7530 | 5540 | 3550 |
| 239 | 597.5 | 9560 | 7570 | 5580 | 3590 |
| 240 | 600.0 | 9600 | 7610 | 5620 | 3630 |
| 241 | 602.5 | 9640 | 7650 | 5660 | 3670 |
| 242 | 605.0 | 9680 | 7690 | 5700 | 3710 |
| 243 | 607.5 | 9720 | 7730 | 5740 | 3750 |
| 244 | 610.0 | 9760 | 7770 | 5780 | 3790 |
| 245 | 612.5 | 9800 | 7810 | 5820 | 3830 |
| 246 | 615.0 | 9840 | 7850 | 5860 | 3870 |
| 247 | 617.5 | 9880 | 7890 | 5900 | 3910 |
| 248 | 620.0 | 9920 | 7930 | 5940 | 3950 |
| 249 | 622.5 | 9960 | 7970 | 5980 | 3990 |
| 250 | 625.0 | 10000 | 8010 | 6020 | 4030 |
| 251 | 627.5 | 10040 | 8050 | 6060 | 4070 |
| 252 | 630.0 | 10080 | 8090 | 6100 | 4110 |
| 253 | 632.5 | 10120 | 8130 | 6140 | 4150 |
| 254 | 635.0 | 10160 | 8170 | 6180 | 4190 |
| 255 | 637.5 | 10200 | 8210 | 6220 | 4230 |
| 256 | 640.0 | 10240 | 8250 | 6260 | 4270 |
| 257 | 642.5 | 10280 | 8290 | 6300 | 4310 |
| 258 | 645.0 | 10320 | 8330 | 6340 | 4350 |
| 259 | 647.5 | 10360 | 8370 | 6380 | 4390 |
| 260 | 650.0 | 10400 | 8410 | 6420 | 4430 |
| 261 | 652.5 | 10440 | 8450 | 6460 | 4470 |
| 262 | 655.0 | 10480 | 8490 | 6500 | 4510 |
| 263 | 657.5 | 10520 | 8530 | 6540 | 4550 |
| 264 | 660.0 | 10560 | 8570 | 6580 | 4590 |
| 265 | 662.5 | 10600 | 8610 | 6620 | 4630 |
| 266 | 665.0 | 10640 | 8650 | 6660 | 4670 |
| 267 | 667.5 | 10680 | 8690 | 6700 | 4710 |
| 268 | 670.0 | 10720 | 8730 | 6740 | 4750 |
| 269 | 672.5 | 10760 | 8770 | 6780 | 4790 |
| 270 | 675.0 | 10800 | 8810 | 6820 | 4830 |
| 271 | 677.5 | 10840 | 8850 | 6860 | 4870 |
| 272 | 680.0 | 10880 | 8890 | 6900 | 4910 |
| 273 | 682.5 | 10920 | 8930 | 6940 | 4950 |
| 274 | 685.0 | 10960 | 8970 | 6980 | 4990 |
| 275 | 687.5 | 11000 | 9010 | 7020 | 5030 |
| 276 | 690.0 | 11040 | 9050 | 7060 | 5070 |
| 277 | 692.5 | 11080 | 9090 | 7100 | 5110 |
| 278 | 695.0 | 11120 | 9130 | 7140 | 5150 |
| 279 | 697.5 | 11160 | 9170 | 7180 | 5190 |
| 280 | 700.0 | 11200 | 9210 | 7220 | 5230 |
| 281 | 702.5 | 11240 | 9250 | 7260 | 5270 |
| 282 | 705.0 | 11280 | 9290 | 7300 | 5310 |
| 283 | 707.5 | 11320 | 9330 | 7340 | 5350 |
| 284 | 710.0 | 11360 | 9370 | 7380 | 5390 |
| 285 | 712.5 | 11400 | 9410 | 7420 | 5430 |
| 286 | 715.0 | 11440 | 9450 | 7460 | 5470 |
| 287 | 717.5 | 11480 | 9490 | 7500 | 5510 |
| 288 | 720.0 | 11520 | 9530 | 7540 | 5550 |
| 289 | 722.5 | 11560 | 9570 | 7580 | 5590 |
| 290 | 725.0 | 11600 | 9610 | 7620 | 5630 |
| 291 | 727.5 | 11640 | 9650 | 7660 | 5670 |
| 292 | 730.0 | 11680 | 9690 | 7700 | 5710 |
| 293 | 732.5 | 11720 | 9730 | 7740 | 5750 |
| 294 | 735.0 | 11760 | 9770 | 7780 | 5790 |
| 295 | 737.5 | 11800 | 9810 | 7820 | 5830 |
| 296 | 740.0 | 11840 | 9850 | 7860 | 5870 |
| 297 | 742.5 | 11880 | 9890 | 7900 | 5910 |
| 298 | 745.0 | 11920 | 9930 | 7940 | 5950 |
| 299 | 747.5 | 11960 | 9970 | 7980 | 5990 |
| 300 | 750.0 | 12000 | 10010 | 8020 | 6030 |

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. A method to facilitate capturing samples as pertain to an object to be imaged, comprising:
   providing N pulsed sampling chains wherein N is an integer greater than 1, where the sampling chains are in planes substantially parallel to each other and substantially equidistant from each other by a given distance, wherein a ratio of the given distance to a desired sample interval is approximately an integer that is relatively prime to N, such that a complete set of samples of the object are captured by the sampling chains as a plurality of sampled images in a single pass notwithstanding that the object and the sampling chains are moving with respect to one another and wherein at least some of the sampled images contain object content that is exclusive to only one of the sampled images.

2. The method of claim 1 wherein N is at least 3.

3. The method of claim 1 wherein the sampling chains are fixed in place and the object is moving past the sampling chains.

4. The method of claim 1 further comprising:
   using the sampling chains to capture the complete set of samples in a corresponding chronological order;
   reordering the samples in other than the chronological order of capture to provide reordered samples;
   using the reordered samples to provide an image of the object.

5. The method of claim 1 further comprising:
   determining a relative velocity as between the object and the sample chains;
   using the relative velocity to determine when to pulse the sampling chains to capture corresponding samples of the object.

6. The method of claim 5 wherein determining the relative velocity comprises measuring the relative velocity.

7. The method of claim 1 wherein providing the sampling chains comprises providing at least one sampling chain having at least two side-by-side detector arrays.

8. The method of claim 7 wherein providing the sampling chains comprises providing sampling chains that each have at least two side-by-side detector arrays.

9. The method of claim 1 wherein the sampling chains each have sides and wherein providing the sampling chains comprises providing sampling chains that each have side-scatter shielding on the sides of the chains to reduce acceptance of scattered signal from out of the plane of the sampling chain.

10. A high-energy-based sample-capture apparatus comprising:

N pulsed sampling chains, where N is an integer greater than 1, where the sampling chains are in planes substantially parallel to each other and substantially equidistant from each other by a given distance, wherein a ratio of the given distance to a desired sample interval is approximately an integer that is relatively prime to N, such that a complete set of samples of an object are captured by the sampling chains as a plurality of sampled images in a single pass notwithstanding that the object and the sampling chains are moving with respect to one another and wherein at least some of the sampled images contain object content that is exclusive to only one of the sampled images.

11. The apparatus of claim 10 wherein N is at least 3.

12. The apparatus of claim 10 wherein the sampling chains are fixed in place during use.

13. The apparatus of claim 10 further comprising:
a control circuit that is communicatively coupled to the sampling chains and that is configured to control pulsed energization of the sampling chains.

14. The apparatus of claim 13 further comprising:
a velocity-measuring component that is communicatively coupled to the control circuit;
and wherein the control circuit is further configured to control the pulsed energization as a function of relative velocity between the object and the sampling chains as measured by the velocity-measuring component.

15. The apparatus of claim 10 wherein at least one of the sampling chains has at least two side-by-side detector arrays.

16. The apparatus of claim 15 wherein each of the sampling chains has at least two side-by-side detector arrays.

17. The apparatus of claim 16 wherein each of the sampling chains has only two side-by-side detector arrays.

18. The apparatus of claim 13 further comprising:
a memory communicatively coupled to receive and store samples of the object from the sampling chains.

19. The apparatus of claim 10 further comprising:
side-scatter shielding disposed on either side of each of the sampling chains to reduce acceptance of scattered signal from out of the plane of the sampling chain.

* * * * *